United States Patent

Hanson et al.

[11] Patent Number: 5,198,109
[45] Date of Patent: Mar. 30, 1993

[54] DIFFUSION CELL

[75] Inventors: William A. Hanson, Westlake Village; Steven W. Shaw, Thousand Oaks, both of Calif.

[73] Assignee: Hanson Research Corp., Chatsworth, Calif.

[21] Appl. No.: 856,350

[22] Filed: Mar. 23, 1992

[51] Int. Cl.$^5$ ............................................. G01N 13/00
[52] U.S. Cl. .............................. 210/321.75; 73/64.47; 210/321.84
[58] Field of Search .......... 210/321.84, 321.6, 644.645, 210/321.75; 73/64.3

[56] References Cited

U.S. PATENT DOCUMENTS 4,594,884 6/1986 Bondi et al. ..................... 210/321.84

*Primary Examiner*—Frank Sever
*Attorney, Agent, or Firm*—Jack C. Munro

[57] ABSTRACT

A diffusion cell to facilitate the automated removal of test aliquots of liquid from a receptor chamber of the diffusion cell so as to determine percutanous absorption through a membrane of a donor fluid from a donor chamber into the receptor chamber of the diffusion cell. There is utilized a sampling port through which the test aliquot is to be removed, the removal being achieved by means of a sample tube which is to be movable into and out of the receptor chamber. Within the receptor chamber is located a stirring device in the form of a helical coil which is to be rotated to achieve stirring and homogeneous mixing of the liquid within the receptor chamber. A refilling tube connects also with the receptor chamber to add liquid into the receptor chamber as the test aliquot has been removed. A leveling tube within the sampling port is to restore the initial preset receptor liquid volume between sampling intervals.

8 Claims, 1 Drawing Sheet

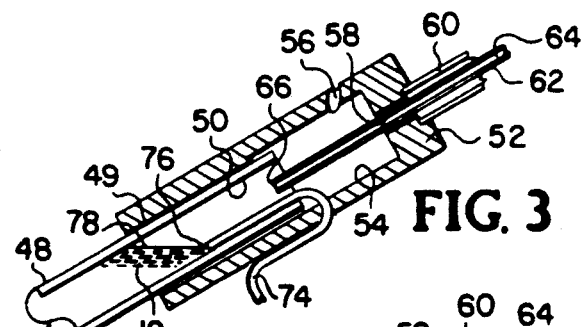
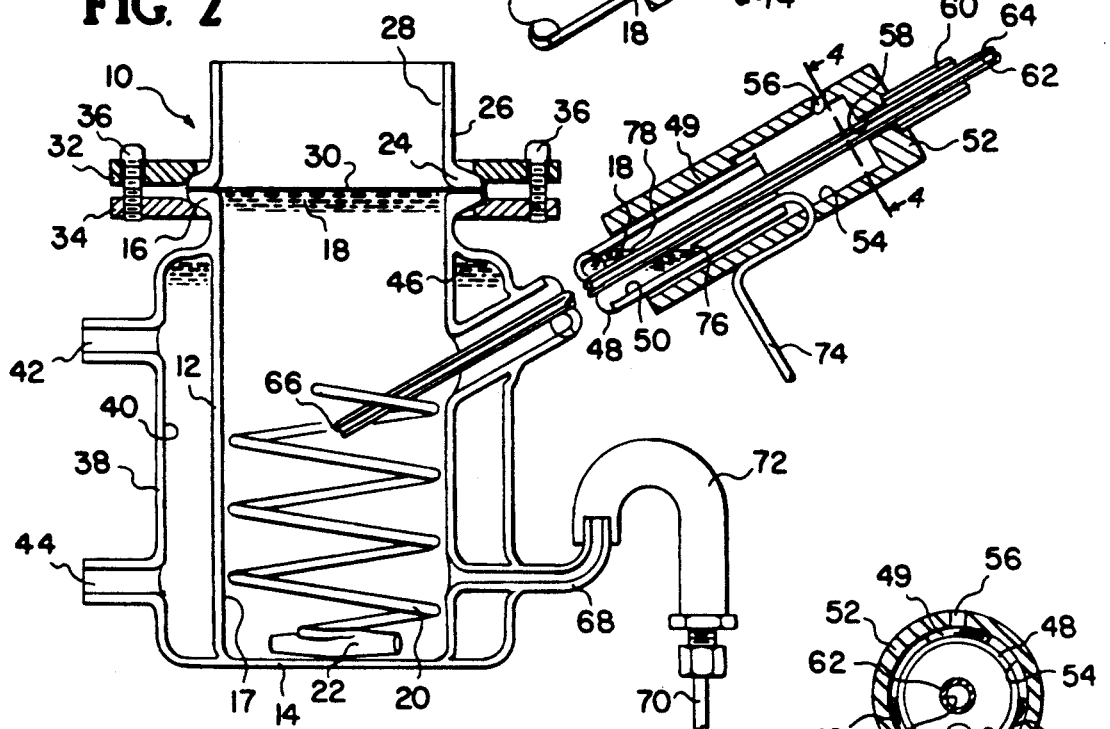
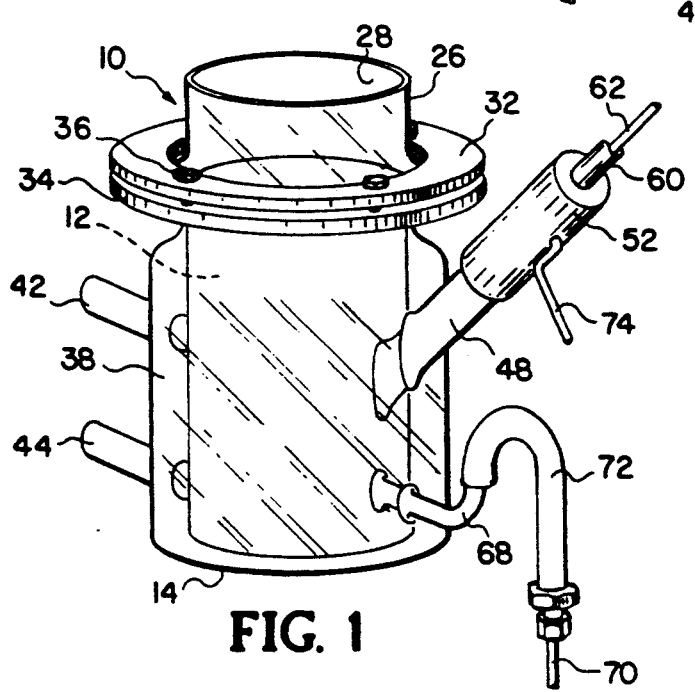

DIFFUSION CELL

BACKGROUND OF THE INVENTION

1. Field of the Invention

The field of this invention relates to testing equipment and more particularly to an apparatus which is useable to determine the transfer of a substance through a membrane into a liquid placed in contact with the opposite side of the membrane.

2. Description of Prior Art

Percutaneous absorption test cells are used in the study of kinetics of the partition coefficients defining the passage and equilibrium of components from one side to the other side of a barrier separatinq two dissimilar substances. A typical test cell is known as the "Franz" cell. The Franz cell is in the form of a container with an upper half separated from a lower half by a porous membrane comprising a barrier. A clamping arrangement is located between the upper half and the lower half with the barrier in the form of a thin sheet material film to be placed and clamped tightly in a stretched configuration by a clamping means located between the upper half and lower half of the Franz cell.

The lower half of the Franz cell container is completely filled with a receptor liquid with this liquid to be in contact with the barrier. Within the upper half is to be placed a donor substance which may comprise a solid, semi-solid, gas or liquid. The receptor normally comprises water, a buffered solution or a saline solution. Connecting with the lower half is a sample port and it is through this sample port that aliquots are to be removed. An aliquot is defined as an exact sub-volume of the overall volume of the receptor liquid. This sample port, in the Franz cell, may also be used to add additional receptor liquid.

While generally useful in the whole field of physical chemistry, Franz cells have become particularly useful in the healthcare field. Transfer kinetics of active substances through the human skin must be determined. Levels of epidermal exposure to pesticides, chemicals, ointments and cosmetics are important in the field of environmental science.

Also, the usage by human beings of prolonged release medications depends on the specific knowledge of a secure prediction of the transfer kinetics a active ingredients penetrate through the skin. Medicinal skin patches have been used for some time by human beings and every year a greater number of such patches are being used. It is necessary to know exactly the amount of active ingredients that will penetrate the user skin within a given amount of time. This information is essential to determine the size of the skin patch and the amount of dosage.

Within a Franz cell, typically the test is conducted by placing the donor material against the total area of the barrier. A typical donor material would be a medicated ointment. A receptor fluid, such as a saline solution, is placed within the receptor chamber in contact with the barrier. All air bubbles are to be removed from the receptor liquid so there is not any air bubble in contact with the barrier as such air bubbles will affect inaccurately the transfer characteristics. There is a stirring device utilized within the receptor chamber which is operated to homogeneously intermix the donor substance as it permeates the membrane into the receptor chamber. At predetermined intervals, aliquots are withdrawn through the sample port for analysis. After an aliquot is withdrawn, such is replaced by an equivalent amount of fresh receptor fluid.

In removing of the aliquot, it is important that the volume removed is not so great as to decrease the overall volume of the receptor fluid to the point to where air would be permitted to enter the receptor chamber. If the desired sample volume is large enough to lower receptor volume to allow bubbles to enter the cell, it is necessary to add replacement fluid between withdrawals. If there is only a single Franz cell utilized and the removal of the aliquot is accomplished manually, generally it would be easy for the user to ensure that the volume would be not so great as to permit air to enter the receptor chamber. However, in common practice, the withdrawal of the aliquots is accomplished from an array of Franz cells with an aliquot being removed from each Franz cell. Therefore the causing of air to enter the receptor chamber can occur rather easily. The reason that a plurality of Franz cells are utilized is to provide a plurality of readings of a quantity of donor substance that penetrates the barrier within a given period of time and then to take an overall average so as to arrive at accurately as possible the transfer characteristics of the active ingredients of the donor substance into the receptor fluid.

After the aliquot is withdrawn, as previously mentioned, an equal quantity of fresh receptor fluid is to be then supplied to each Franz cell. When the fresh receptor fluid is to be supplied, a given period of time must occur so that the stirring device will evenly mix the new receptor fluid with the receptor liquid that is contained within the receptor chamber. In order to provide adequate time to evenly mix the fresh receptor fluid with the older receptor fluid, it is common to permit as much as thirty minutes for homogeneous intermixing to occur. It is frequently desirable to remove aliquots spaced only a few minutes from each other. Therefore, the time of achieving homogeneous intermixture of thirty minutes is just not acceptable.

SUMMARY OF THE INVENTION

One of the objectives of the present invention is to construct a diffusion cell which provides for the withdrawal of aliquots in a manner that does not permit air to be added into the receptor chamber.

Another objective of the present invention is to construct a diffusion cell which provides for accurate replacement in volume of fresh receptor fluid equal to what was withdrawn in each aliquot.

Another objective of the present invention is to construct a diffusion cell which utilizes an improved stirring device within the receptor chamber to restore homogeneity more rapidly within the receptor chamber after fresh receptor fluid has been added.

Another objective of the present invention is to construct a diffusion cell which enables the aliquot volume to exceed the volume of the sample port with this being accomplished by affecting the removal and replacement simultaneously rather than sequentially.

Another objective of the present invention is to utilize a novel apparatus within the receptor chamber to provide rapid restoration of equilibrium and homogeneity within the receptor chamber which reduces the time increment between aliquots.

The diffusion cell of the present invention is in the form of a container which is divided between a bottom portion and a top portion. In between the bottom portion and the top portion is clamped a barrier formed of sheet material which is sufficiently porous to permit the transmission of a substance thereto. Within the bottom portion is a receptor chamber which is to be filled with the receptor liquid. The top portion includes a donor chamber within which is to be located a donor substance which is to be spread evenly across the barrier. Within the receptor chamber is located a helical coil which is to be magnetically rotatably driven so as to function as a stirring apparatus. The length of the coil is at least one half the height of the receptor chamber. Connecting to the receptor chamber through the sidewall thereof is a sample port. Associated with the sample port is a sample tube with this sample tube to be moveable to an inward position locating the sample tube within the receptor chamber to facilitate the removing of aliquots of the receptor media. The sample tube can be moved to a retracted position which is spaced from the receptor chamber. This is the position of the sample tube during the time that aliquots are not being taken. Also associated with the sample tube is an overflow or leveling tube so if a greater quantity of receptor media is supplied within the receptor chamber than what is withdrawn as an aliquot sample, this excessive amount of media will be caused to flow through this overflow tube maintaining an exact receptor volume. Also located through the sidewall of the receptor chamber is a refilling tube through which fresh media is to be added to the receptor media when desired. The refilling tube is spaced furthest from the barrier and directly adjacent the bottom surface of the receptor chamber. The sample tube is located approximately midway between the refilling tube and the barrier. The receptor chamber is encased in a jacket through which liquid is to be supplied at a certain temperature so the receptor media will be caused to assume that temperature regardless of ambient temperature.

BRIEF DESCRIPTION OF THE DRAWING

FIG. 1 is an exterior isometric view of the diffusion cell of the present invention showing the sample tube within the diffusion cell located in the retracted position;

FIG. 2 is a cross-sectional view taken along a vertical plane through the diffusion cell of FIG. 1 showing the sample tube in the sample withdrawing position;

FIG. 3 is a view of the outer end of the sample tube utilized in conjunction with the diffusion cell of the present invention showing the sample tube in the retracted position which is also the position of FIG. 1; and FIG. 4 is a cross-sectional view taken through the sample tube arrangement of the diffusion cell of the present invention taken along line 4—4 of FIG. 2.

DETAILED DESCRIPTION OF THE SHOWN EMBODIMENT

Referring particularly to the drawing, there is shown in FIG. 1 the diffusion cell 10 of this invention. The diffusion cell 10 comprises a thin-walled cylindrical container 12 which has a closed bottom 14 and an open top defined by an outwardly flared annular flange 16. The container 12 has an internal chamber 17 which is to be filled with a receptor liquid 18. The receptor liquid 18 comprises a liquid such as water, saline or other similar type of solution.

Placed within the chamber 17 is a helical coil 20 which has a free upper end and at the lower end is attached to metallic elongated rod 22. Rod 22 is to be attracted to a magnet (not shown) which is to be located exteriorly of the container 10 and actually directly adjacent bottom 14. Rotation of this magnet will result in rotation of the rod 22 and simultaneous rotation of the coil 20. The coil 20 is of a length at least as great as one half the height of the chamber 16. It has been found that the stirring action caused by the coil 20 within the receptor liquid 18 is exceedingly effective and within a matter of just a few minutes will cause the liquid 18 to be homogeneous.

Abutting against the flange 16 is an annular flange 24 of a donor housing 26 which has an internal donor chamber 28. This chamber 28 is shown to be open at its upper end to the ambient. Tightly stretched across the width of the aligned chambers 17 and 28 is a thin sheet material barrier 30. This barrier 30 is fixedly held in position between the flanges 16 and 24 by means of a clamping mechanism in the form of a pair of plates 32 and 34. Interconnecting the plates 32 and 34 are a series of threaded fasteners in the form of bolts 36. Tightening of the bolts 36 will produce the clamping action tending to tightly clamp together the flanges 16 and 24.

Typical material for the barrier 30 can be any desired material. Frequently, a desireable form of material for the barrier 30 would be a material that would essentially duplicate human skin. There are some plastics that are known that do duplicate human skin rather closely. It is also possible that human skin could be utilized for the barrier 30 as well as other types of organic material. Also other types of synthetic material other than plastics could be utilized such as possibly a tightly woven cloth material.

It is desireable to have the receptor liquid 18 maintained at a specifically known temperature level. One convenient method to achieve this, surrounding the container 12 is a jacket 38 which has an internal jacket chamber 40. Connecting with the chamber 40 is an inlet 44 and an outlet 42. A liquid 46 to be supplied through the inlet 42 and caused to circulate within the chamber 40 and then exit through the outlet 42. With the liquid 46 being at a pre-established temperature, it can be readily seen that the receptor liquid 18 will be caused to quickly also assume that temperature.

Integrally connected to the wall of the container 1 is a sample port 48. This sample port 48 is open at its outer end and has an internal chamber 50. Fixedly mounted around the outer end of the sample port 48 is a cap 52. The cap 52 has an internal chamber 54 within which the open outer end of the sample port 48 is located. The cap 52 is fixed onto the exterior surface of the sample port 48 and plurality of spacer blocks 49. The cap 52 includes a hole 56 so that ambient air pressure can be applied against the liquid 18 that rises to the level shown within FIGS. 2 and 3 of the drawing. This level of the liquid 18 is in alignment with the barrier 30 since the liquid 18 must be in contact with the barrier 30.

The outer end of the cap 52 includes a hole 58. Fixedly mounted to the exterior wall surface of the cap 52 around the hole 58 is a guide tube 60. Movably mounted within the guide tube 60 and extending through the hole 58 is a sample tube 62. The sample tube 62 has an internal passageway 64. This sample tube 62 has an inner end 66.

The sample tube 62 is to be movable within the guide tube 60 so that the end 66 can be located in the sample-taking position as shown in FIG. 2 in the internal chamber 17. This sample tube 62 can be positioned in the retracted position spaced exteriorly of the liquid 18 which is shown in FIG. 3. With the tube 62 in the position shown in FIG. 2, a known quantity of the liquid 18 is to flow through the passage 64 to then be deposited to the appropriate collecting container (not shown). Normally, the quantity of aliquot extracted through the sample tube 62 comprises several hundred microliters.

If the volume of the aliquot is substantial, it would be possible to lower the level of the liquid 18 so that air bubbles would be caused to enter the chamber 17 and come to rest against the lower surface of the barrier 30. This is to be prevented and, in order to absolutely prevent this, it is desireable to simultaneously refill with new liquid the chamber 17 as the aliquot is removed by the sample tube 62. However, it is important that the new liquid that is being supplied does not mix with the portion of the liquid that is being extracted through the sample tube 62. In order to achieve this end result, a refilling port 68 is integrally connected to the wall of the container 12 with this refilling port 68 being located directly adjacent the bottom 14 and spaced some distance from the inner end of the tube 66 during the time that this aliquot is being taken. Fresh new liquid is to be supplied from a source (not shown) through supply tube 70, hose 72 into refilling port 68 and hence into the chamber 17.

It is normally designed for the refilling liquid be supplied to the refilling port 68 to be of the precise same volume of the aliquot that is being withdrawn by the sample tube 62. If, per chance, a slightly greater amount of liquid is supplied through the refilling tube 68, there will be a certain amount of excess that would be created. Mounted within the internal chamber 50 of the sample port 48 is an overflow or leveling tube 74 with this overflow tube 74 terminating in an inner end 76. This inner end 76 is to be positioned precisely at the surface 78 of the liquid within the internal chamber 50 of the sample tube 48. The heigth of the surface 78 is to be at the same horizontal plane as the barrier 30. Therefore, any excess liquid 18 would be caused to flow through the overflow tube 74 and be extracted. In actual practice, a vacuum may be supplied continuously to the overflow tube 74 in order to facilitate the removal of this excess. Also, a pump is to be connected with the conduit 70, which is not shown, with this pump functioning to add under pressure the refilling fresh portion of the liquid.

What is claimed is:

1. A diffusion cell comprising:
a chamber divided by a membrane into a donor chamber and a receptor chamber, a liquid filling said receptor chamber and being in contact with said membrane, a media to be supplied into said donor chamber with said media being permitted to diffuse through said membrane and mixed with said liquid;
a sample port connecting with said receptor chamber, said sample port permitting removal of a quantity of said liquid;
a refilling port connecting with said receptor chamber, said refilling port permitting supplying of an additional quantity of said liquid into said receptor chamber; and
said receptor chamber including a mixing device, said mixing device to be operated to effect even mixing of said liquid within said receptor chamber, said mixing device comprising a helical coil of a length equal to at least one half the length of said receptor chamber.

2. The diffusion cell as defined in claim 1 wherein:
said membrane being mounted on a clamping means, said clamping means being located between said donor chamber and said receptor chamber, said clamping means being disengagable to effect removal and replacement of said member.

3. The diffusion cell as defined in claim 1 wherein:
said donor chamber being located at a higher elevation than said receptor chamber.

4. The diffusion cell as defined in claim 1 wherein:
said sample port connecting with said receptor chamber in between said refilling port and said membrane.

5. The diffusion cell as defined in claim 1 wherein:
said mixing device including a magnetizable member adapted to be moved by a magnet located exteriorly of said receptor chamber.

6. A diffusion cell comprising:
a chamber divided by a membrane into a donor chamber and a receptor chamber, a liquid filling said receptor chamber and being in contact with said membrane, a media to be supplied into said donor chamber with said media being permitted to diffuse through said membrane and mixed with said liquid;
a sample port connecting with said receptor chamber, said sample port permitting removal of a quantity of said liquid; and
a refilling port connecting with said receptor chamber, said refilling port permitting supplying of an additional quantity of said liquid into said receptor chamber,
a sample tube mounted in conjunction with said sample port, said sample tube being movable between an inward position and an outward position, with said sample tube in said inward position said sample tube is located within said receptor chamber thereby facilitating removal of a quantity of said liquid, with said sample tube in said outward position said sample tube being spaced from said receptor chamber thereby not being usable to remove a quantity of said liquid.

7. The diffusion cell as defined in claim 6 wherein:
an overflow tube connecting with said sample port, said overflow tube functioning to remove excess said liquid from said sample port so as to maintain the level of said liquid within said sample port at a precise position prior to removal of quantity of said liquid by said sample tube.

8. The diffusion cell as defined in claim 7 wherein:
said level maintained by said overflow tube being located between said inward and outward position of said sample tube.

* * * * *